(12) United States Patent
Friedlander et al.

(10) Patent No.: US 8,972,406 B2
(45) Date of Patent: Mar. 3, 2015

(54) GENERATING EPIGENETIC COHORTS THROUGH CLUSTERING OF EPIGENETIC SURPRISAL DATA BASED ON PARAMETERS

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 357 days.

(21) Appl. No.: 13/563,072

(22) Filed: Jul. 31, 2012

(65) Prior Publication Data

US 2014/0006447 A1 Jan. 2, 2014

Related U.S. Application Data

(63) Continuation-in-part of application No. 13/537,385, filed on Jun. 29, 2012.

(51) Int. Cl.
*G06F 17/30* (2006.01)
*G06F 19/24* (2011.01)
*G06F 19/18* (2011.01)

(52) U.S. Cl.
CPC .......... *G06F 17/30864* (2013.01); *G06F 19/24* (2013.01); *G06F 19/18* (2013.01)
USPC ............ 707/737; 707/776; 702/719; 702/720

(58) Field of Classification Search
CPC ................................................ G06F 17/30864
USPC ........................................................ 707/737
See application file for complete search history.

(56) References Cited

U.S. PATENT DOCUMENTS 6,401,043 B1 6/2002 Stanton, Jr.
6,468,744 B1 10/2002 Cronin (Continued)

FOREIGN PATENT DOCUMENTS

CN 101430742 A 5/2009
CN 102081707 A 6/2011

(Continued)

OTHER PUBLICATIONS

Abe, Hidenao et al., "Implementing an Integrated Time-Series Data Mining Environment Based on Temporal Pattern Extraction Methods: A Case Study of an Interferon Therapy Risk Mining for Chronic Hepatitis," 2006, Springer Berlin Heidelberg, New Frontiers in Artificial Intelligence, Lecture Notes in Computer Science, vol. 4012, pp. 425-435.*

(Continued)

*Primary Examiner* — Robert Beausoliel, Jr.
*Assistant Examiner* — Richard Bowen
(74) *Attorney, Agent, or Firm* — Brown & Michaels, PC; John R. Pivnichny

(57) ABSTRACT

A method, computer program product, and system generating epigenetic cohorts for a specific time period through clustering of epigenetic surprisal data at a specific time comprising. receiving a phenotypic and/or demographic parameter and a cluster characteristics input from a user; searching the epigenetic surprisal data at a specific time for the parameter and storing matches in a repository; generating a cluster comprising a centroid for each parameter by populating the cluster based on the matches of the parameter with the epigenetic surprisal data at a specific time period; determining at least two epigenetic cohorts for a specific time period from the cluster for each parameter and based on the input from the user; and if the cohorts do not match the input of the user, reporting the cohorts determined to the user and returning to the step of receiving a parameter and characteristic input from a user.

18 Claims, 7 Drawing Sheets

(56) References Cited

U.S. PATENT DOCUMENTS

| | | | |
|---|---|---|---|
| 6,609,085 | B1 | 8/2003 | Uemura et al. |
| 7,017,186 | B2 | 3/2006 | Day |
| 8,012,740 | B2 | 9/2011 | Hillis |
| 8,055,603 | B2 | 11/2011 | Angell et al. |
| 8,078,407 | B1* | 12/2011 | Brown .................. 702/19 |
| 8,126,655 | B2 | 2/2012 | Katoh et al. |
| 8,145,582 | B2 | 3/2012 | Angell et al. |
| 8,296,268 | B2 | 10/2012 | Ingles |
| 8,340,914 | B2 | 12/2012 | Gatewood |
| 2003/0194711 | A1 | 10/2003 | Zapala |
| 2003/0195706 | A1 | 10/2003 | Korenberg |
| 2003/0220844 | A1 | 11/2003 | Marnellos |
| 2003/0233197 | A1* | 12/2003 | Padilla et al. ............ 702/20 |
| 2004/0153255 | A1 | 8/2004 | Ahn |
| 2004/0224334 | A1 | 11/2004 | Shibuya |
| 2005/0019787 | A1 | 1/2005 | Berno et al. |
| 2005/0267693 | A1 | 12/2005 | Allard et al. |
| 2006/0020398 | A1* | 1/2006 | Vernon et al. ............ 702/20 |
| 2006/0112264 | A1 | 5/2006 | Agarwal |
| 2006/0166224 | A1 | 7/2006 | Norviel |
| 2007/0276610 | A1 | 11/2007 | Korenberg |
| 2007/0282538 | A1 | 12/2007 | Narasimhan et al. |
| 2008/0077607 | A1 | 3/2008 | Gatawood et al. |
| 2008/0154512 | A1 | 6/2008 | Leong |
| 2008/0294692 | A1 | 11/2008 | Angell et al. |
| 2009/0006002 | A1 | 1/2009 | Honisch |
| 2009/0018994 | A1 | 1/2009 | Hajdukiewicz |
| 2009/0158211 | A1* | 6/2009 | Gogolak .................. 715/811 |
| 2009/0182862 | A1 | 7/2009 | Thomson |
| 2010/0241670 | A1 | 9/2010 | Justice |
| 2011/0029341 | A1 | 2/2011 | Muse et al. |
| 2011/0087436 | A1 | 4/2011 | Klapa |
| 2011/0213212 | A1 | 9/2011 | Al-Ali |
| 2011/0319298 | A1 | 12/2011 | Benner et al. |
| 2012/0066001 | A1 | 3/2012 | Sanborn |
| 2012/0185612 | A1 | 7/2012 | Zhang et al. |
| 2012/0197533 | A1 | 8/2012 | Nazarenko |
| 2012/0230326 | A1 | 9/2012 | Ganeshalingam et al. |
| 2013/0024435 | A1 | 1/2013 | Poirier et al. |
| 2013/0262465 | A1* | 10/2013 | Galle et al. ............... 707/737 |

FOREIGN PATENT DOCUMENTS

| | | |
|---|---|---|
| CN | 102222174 A | 10/2011 |
| JP | 2004240975 | 8/2004 |
| WO | 02063479 A1 | 8/2002 |
| WO | 03081509 A2 | 10/2003 |
| WO | 03083442 A2 | 10/2003 |
| WO | 2005107412 A2 | 11/2005 |
| WO | 2010072382 A2 | 7/2010 |
| WO | 2011076130 A1 | 6/2011 |

OTHER PUBLICATIONS

Centroid definition, "The Penguin Dictionary of Mathematics" 2008.

Kohane, I et al.; "Health Information Identification and De-Identification Toolkit"; Proc AMIA Symp.; 1998; pp. 356-360.

Malin, B.; "An Evaluation of the Current State of Genomic Data Privacy Protection Technology and a Roadmap for the Future"; J Am Med Inform Assoc.; Dec. 2005; pp. 28-34.

Kapis, K. et al.; "Security Mechanisms for Electronic Patient Records in Mobile Intelligent Services"; MEDINF; Craiova Medicala Journal; Oct. 2003; 4 Pages.

Heurix, J. et al.; "A Hybrid Approach Integrating Encryption and Pseudonymization for Protecting Electronic Health Records"; Proceedings of the Eighth IASTED International Conference on Biomedical Engineering; 2011; 8 pages.

Weerasinghe, D. et al.; "Securing electronic health records with novel mobile encryption schemes"; Int. J. Electronic Healthcare; 2007, vol. 3 No. 4; pp. 395-416.

Dean, J. et al; MapReduce: Simplified Data Processing on Large Clusters; OSDI; 2004; pp. 1-13.

Hedlund, B.; Understanding Hadoop Clusters and the Network; http://bradhedlund.com/?p=3108; Sep. 10, 2011; 26 pages.

Titmus, M. et al.; Answering the demands of digital genomics; Concurrency and Computation: Practice and Experience; Aug. 2012; 12 pages.

Schadt, E et al.; Computational solutions to large-scale data management and analysis; Nat. Rev. Genet; Sep. 2010; 22 pages.

Shvachko, K. et al.; The Hadoop Distributed File System; IEEE; 2010: 10 pages.

International PCT Search Report for PCT/IB2013/055173; Jan. 2, 2014; 9 pages.

Haefliger et al. "Four Novel Members of the Connexin Family of Gap Junction Proteins." The Journal of Biological Chemistry. vol. 267.

PCT Search Report for PCT/IB2013/052012 mailed Aug. 15, 2013; 10 pages.

Craig, A.G. et al; "Ordering of cosmid clones covering the Herpes simplex virus type 1 (HSV-1) genome: a test case for fingerprinting by hybridisation"; Nucleic Acids Research, vol. 18, No. 9; 1990; pp. 2653-2660.

Grumbach, S. et al.; A New Challenge for Compression Algorithms: Genetic Sequences; Genetic Sequences; 1994;12 pages.

International PCT Search Report for PCT/IB2013/052011; Jun. 18, 2013; 8 pages.

Hillman-Jackson, J. et al; "Using Galaxy to Perform Large-Scale Interactive Data Analyses"; Current Protocols in Bioinformatics, Jun. 2012; 47 pages.

Galaxy Wiki; http://wiki.g2.bx.psu.edu/: At least as early as 2011; 2 pages.

Galaxy Wiki; "Custom Genomes"; http://wiki.g2.bx.psu.edu/Learn/CustomGenomes; At least as early as Apr. 2012; 4 pages.

Galaxy—Rous; "Comparing genomic intervals using galaxy"; http://rous.mit.edu/index.php/Comparing_genomic_intervals_using_galaxy; At least as early as Jan. 27, 2010; 2 pages.

The Galaxy Team; "An Introduction to Galaxy"; http://UseGalaxy.org; Jul. 28, 2011; 107 pages.

Christopher Schmid; "Reviews in Computational Biology Comparing Epigenetic Maps: Computational tasks and aspects of data analysis"; Swiss Tropical and Public Health Institute; May 2, 2011; 31 pages.

"ssahaSNP: Sequence Search and Alignment by Hashing Algorithm"; http://www.sanger.ac.uk/resources/software/ssahashp/; Wellcome Trust Sanger Institute; 2011; 2 pages.

He, Q. et al; A Variable Selection Method for Genome-wide Association Studies; Dept. of Biostatistics, Univ. of North Carolina; Oct. 2010; pp. 1-8.

"GWASelect: A Variable Selection Method for Genomewide Association Studies"; http://www.bios.unc.edu/~lin/software/GWASelect; at least as early as Feb. 23, 2010; 1 page.

Ruschendorf, F. et al.; "ALOHOMORA: a tool for linkage analysis using 10K SNP Array Data"; BioInformatics Applications Note; vol. 21, No. 9, 2005; pp. 2123-2125.

Hoffmann K. et al.; "easyLINKAGE-Plus—automated linkage analyses using large-scale SNP data"; BioInformatics Applications Note, vol. 21 No. 17 2005. pp. 3565-3567.

International HapMap Project; http://hapmap.ncbi.nlm.nih.gov/cgi-perl/gbrowse/hapmap27_B36/; Feb. 2009; 2 pages.

International HapMap Project: http://en.wikipedia.org/wiki/International_HapMap_Project; Oct. 27, 2002; 4 pages.

Jorde, L. B. et al.; Genetic variation, classification and 'race'; 2004; Nature Genetics 36 (11 Suppl): S28-S33; 8 pages.

Tishkoff, S. A. et al., Implications of biogeography of human populations for 'race' and medicine; Nature Genetics 36 (11 Suppl): S21-7; 2004; 9 pages.

International HapMap Project; http://hapmap.ncbi.nlm.nih.gov/; 2009; 3 pages.

Human Genome Project Information; http://www.ornl.gov/sci/techresources/Human_Genome/faq/faqs1.shtml; 1990; 9 pages.

Wacker, S.A. et al; Using transcriptome sequencing to identify mechanisms of drug action and resistance; Nature Chemical Biology; Feb. 2012; 37 pages.

Brandon, M.G. et al., "Data structures and compression algorithms for genomic sequence data"; BioInformatics—vol. 25: 2009; pp. 1731-1738.

(56) References Cited

OTHER PUBLICATIONS

Cao, M.D. et al.: "A genome alignment algorithm based on compression"; BMC Cioinformatics; 2010; 16 pages.
Christley, S. et al., "Human genomes as email attachments"; Bio Informatics—vol. 25; 2009; pp. 274-275.
Human Genome Diversity Project; http://wikipedia.org/wiki/Human_Genome_Diversity_Project; 2012; 5 pages.
Cavalli-Sforza, L., "The Human Genome Diversity Project: past, present and future";Nature Reviews/Genetics; Apr. 2005; 8 pages.
Rosenberg, N.A.; "Standardized subsets of the HGDP-CEPH Human Genome Diversity Cell Line Panel, accounting for atypical and duplicated samples and pairs of close relatives"; Annals of Human Genetics; Feb. 2006; 40 pages.
Amigo, J. et al.; SPSmart: adapting population based SNP genotype databases for fast and comprehensive web access; BMC Bioinformatics; Oct. 2008; 6 pages.
Li, J.A. et al. "Worldwide Human Relationships Inferred from Genome-Wide Patterns of Variation"; Science—vol. 319; 2008; 6 pages.
Novembre, J. et al., "Genes mirror geography within Europe"; Nature; Nov. 2008; 13 pages.
Ernst, J. and Bar-Joseph, Z. "Stem: a tool for the analysis of short time series gene expression data." BMC Bioinformatics, 7:191, Apr. 2006.
Ernst, J. et al. "Clustering Short Time Series Gene Expression Data." Bioinformatics, 21 Suppl. 1, pp. i159-i168, Mar. 2005.

\* cited by examiner

GENERATING EPIGENETIC COHORTS THROUGH CLUSTERING OF EPIGENETIC SURPRISAL DATA BASED ON PARAMETERS

CROSS-REFERENCE TO RELATED APPLICATIONS

This is a continuation-in-part of copending application Ser. No. 13/537,385, filed Jun. 29, 2012, entitled "MINIMIZATION OF EPIGENETIC SURPSIAL DATA OF EPIGENETIC DATA WITHIN A TIME SERIES". The aforementioned application is hereby incorporated herein by reference.

BACKGROUND

The present invention relates to epigenetic surprisal data, and more specifically to generating epigenetic cohorts through clustering of epigenetic surprisal data based on parameters such as demographics and phenotypic characteristics.

Epigenetics includes the study of heritable changes in gene expression that are not due to changes in DNA sequence, in other words, all modifications to genes other than changes to the DNA sequence itself. Examples of modifications are DNA methylation, histone modification, chromatic accessibility, acetylation, phosphorylation, ubiquitination, ADP-ribosylation and others. The modifications alter the chromatin structure of the DNA and its accessibility, and therefore the regulation of gene expression patterns. The pattern of gene expression can also be modified by exogenous influences, such as environmental influences including nutrition. These modifications can persist throughout an organism's lifetime and be passed on to future generations.

Epigenetic maps include a map or display of what modifications have been made to specific chromosomes and/or the entire genome of an organism. Epigenetic maps are produced by massively parallel sequencing of a portion of an organism's genome or the entire genome and mapping the sequence to a reference genome assembly to infer genomic coordinates of modifications.

SUMMARY

According to one embodiment of the present invention, a method of generating epigenetic cohorts for a specific time period through clustering of epigenetic surprisal data at a specific time. The method comprising: a computer receiving a phenotypic and/or demographic parameter and a cluster characteristics input from a user; the computer searching the epigenetic surprisal data at a specific time associated with a patient for the phenotypic and/or demographic parameter and storing matches of the parameter with the epigenetic surprisal data in a repository; the computer generating a cluster comprising a centroid for each parameter by populating the cluster based on the matches of the parameter with the epigenetic surprisal data at a specific time period; the computer determining at least two epigenetic cohorts for a specific time period, a control cohort and a treatment cohort, from the cluster for each parameter and based on the input from the user; and if the cohorts do not match the input of the user, reporting the cohorts determined to the user and return to the step of the computer receiving a phenotypic and/or demographic parameter from a user and a cluster characteristics input.

According to another embodiment of the present invention, a computer program product for generating epigenetic cohorts for a specific time period through clustering of epigenetic surprisal data at a specific time. The computer program product comprising: one or more computer-readable, tangible storage devices; program instructions, stored on at least one of the one or more storage devices, to receive a phenotypic and/or demographic parameter and a cluster characteristics input from a user; program instructions, stored on at least one of the one or more storage devices, to search the epigenetic surprisal data at a specific time associated with a patient for the phenotypic and/or demographic parameter and store matches of the parameter with the epigenetic surprisal data in a repository; program instructions, stored on at least one of the one or more storage devices, to generate a cluster comprising a centroid for each parameter by populating the cluster based on the matches of the parameter with the epigenetic surprisal data at a specific time period; program instructions, stored on at least one of the one or more storage devices, to determine at least two epigenetic cohorts for a specific time period, a control cohort and a treatment cohort, from the cluster for each parameter and based on the input from the user; and if the cohorts do not match the input of the user, program instructions, stored on at least one of the one or more storage devices, to report the cohorts determined to the user and return to program instructions, stored on at least one of the one or more storage devices, to receive a phenotypic and/or demographic parameter from a user and a cluster characteristics input.

According to another embodiment of the present invention, a system for generating epigenetic cohorts for a specific time period through clustering of epigenetic surprisal data at a specific time. The system comprising: one or more processors, one or more computer-readable memories and one or more computer-readable, tangible storage devices; program instructions, stored on at least one of the one or more storage devices for execution by at least one of the one or more processors via at least one of the one or more memories, to receive a phenotypic and/or demographic parameter and a cluster characteristics input from a user; program instructions, stored on at least one of the one or more storage devices for execution by at least one of the one or more processors via at least one of the one or more memories, to search the epigenetic surprisal data at a specific time associated with a patient for the phenotypic and/or demographic parameter and store matches of the parameter with the epigenetic surprisal data in a repository; program instructions, stored on at least one of the one or more storage devices for execution by at least one of the one or more processors via at least one of the one or more memories, to generate a cluster comprising a centroid for each parameter by populating the cluster based on the matches of the parameter with the epigenetic surprisal data at a specific time period; program instructions, stored on at least one of the one or more storage devices for execution by at least one of the one or more processors via at least one of the one or more memories, to determine at least two epigenetic cohorts for a specific time period, a control cohort and a treatment cohort, from the cluster for each parameter and based on the input from the user; and if the cohorts do not match the input of the user, program instructions, stored on at least one of the one or more storage devices for execution by at least one of the one or more processors via at least one of the one or more memories, to report the cohorts determined to the user and return to program instructions, stored on at least one of the one or more storage devices, to receive a phenotypic and/or demographic parameter from a user and a cluster characteristics input.

DETAILED DESCRIPTION

The illustrative embodiments recognize that by comparing epigenetic modifications to a reference epigenetic map or a baseline epigenetic map, the data will be reduced down to the "surprisal data" which are "unlikely" or "surprising" relative to a baseline epigenetic map or a reference epigenetic map of modifications. Epigenetic modifications may include, but are not limited to, DNA methylation, histone modification, chromatic accessibility, acetylation, phosphorylation, ubiquitination, and ADP-ribosylation. The epigenetic modifications alter the chromatin structure of the DNA and its accessibility, and therefore the regulation of gene expression patterns.

The illustrative embodiments provide a computer implemented method, apparatus, and computer usable program code for generating epigenetic cohorts at a specific time through clustering of epigenetic surprisal data based on parameters such as demographics and phenotypic characteristics. Results of a clustering process are used to calculate an objective function for selecting an optimal control cohort. A cohort is a group of individuals with common characteristics. Frequently, cohorts are used to test the effectiveness of medical treatments. Treatments are processes, medical procedures, drugs, actions, lifestyle changes, or other treatments prescribed for a specified purpose. A control cohort is a group of individuals that share a common characteristic that does not receive the treatment. The control cohort is compared against individuals or other cohorts that received the treatment to statistically prove the efficacy of the treatment.

The illustrative embodiments provide an automated method, apparatus, and computer usable program code for selecting individuals and their genetic surprisal data for a control cohort. To demonstrate a cause and effect relationship, an experiment must be designed to show that a phenomenon occurs after a certain treatment is given to a subject and that the phenomenon does not occur in the absence of the treatment. A properly designed experiment generally compares the results obtained from a treatment cohort against a control cohort which is selected to be practically identical. For most treatments, it is often preferable that the same number of individuals is selected for both the treatment cohort and the control cohort for comparative accuracy. The classical example is a drug trial. The cohort or group receiving the drug would be the treatment cohort, and the group receiving the placebo would be the control cohort. The difficulty is in selecting the two cohorts to be as near to identical as possible while not introducing human bias.

Figure 1:
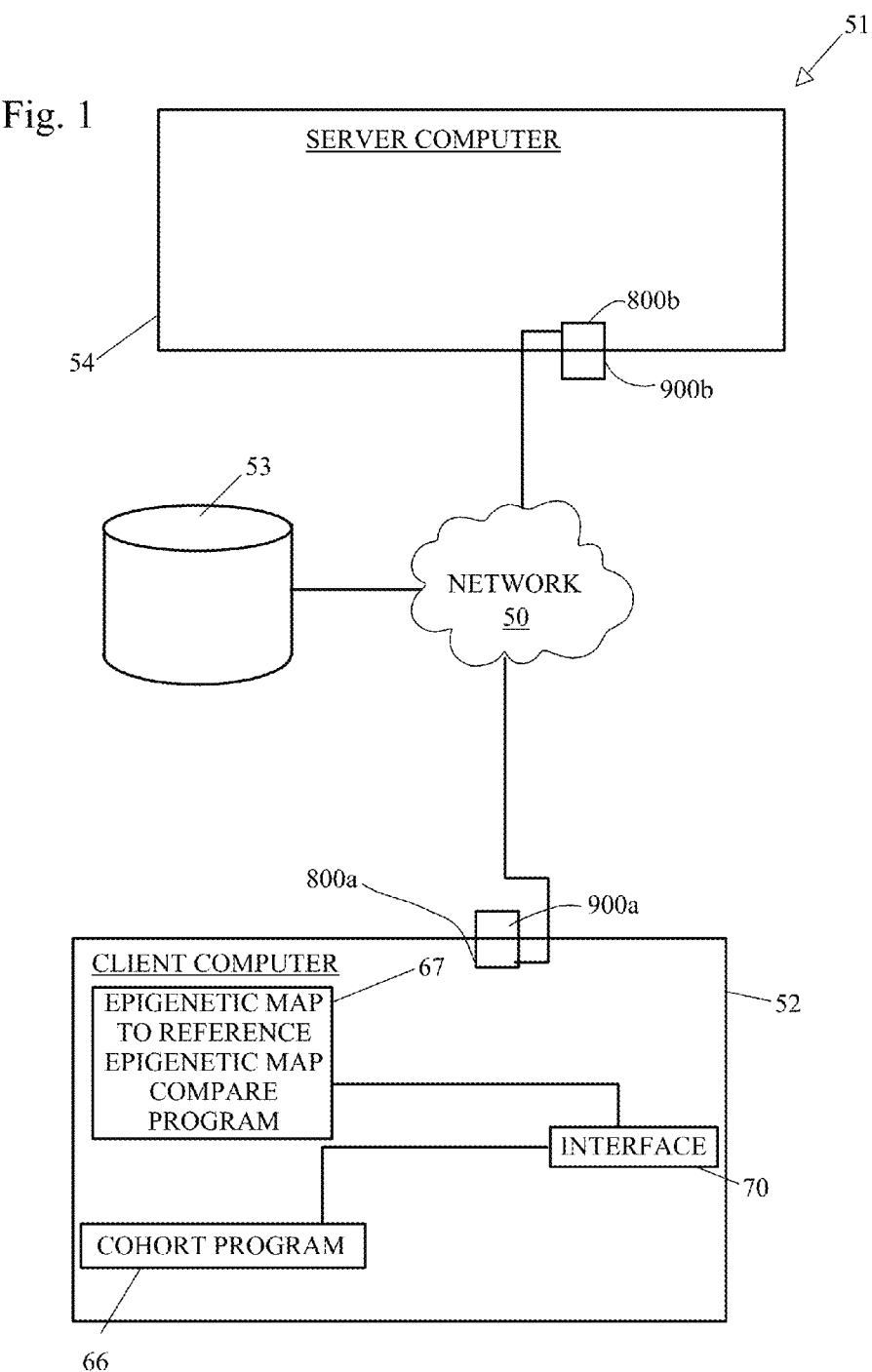
FIG. 1 depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wires, wireless communication links, or fiber optic cables.

In the depicted example, a client computer 52, server computer 54, and a repository 53 connect to network 50. In other exemplary embodiments, network data processing system 51 may include additional client computers, storage devices, server computers, and other devices not shown. The client computer 52 includes a set of internal components 800a and a set of external components 900a, further illustrated in FIG. 7. The client computer 52 may be, for example, a mobile device, a cell phone, a personal digital assistant, a netbook, a laptop computer, a tablet computer, a desktop computer, a sequencing machine or any other type of computing device.

Client computer 52 may contain an interface 70. The interface can be, for example, a command line interface, a graphical user interface (GUI), or a web user interface (WUI). The interface may be used, for example for viewing a reference epigenetic map, epigenetic surprisal data, clusters, cohorts, and Kohonen feature maps. The interface may also accept an input regarding a number of cohorts, a number of clusters, cluster size, density of the clusters, phenotypic parameters, demographic parameters, and the reference epigenetic map.

In the depicted example, server computer 54 provides information, such as boot files, operating system images, and applications to client computer 52. Server computer 54 can compute the information locally or extract the information from other computers on network 50. Server computer 54 includes a set of internal components 800b and a set of external components 900b illustrated in FIG. 7.

Figure 7:
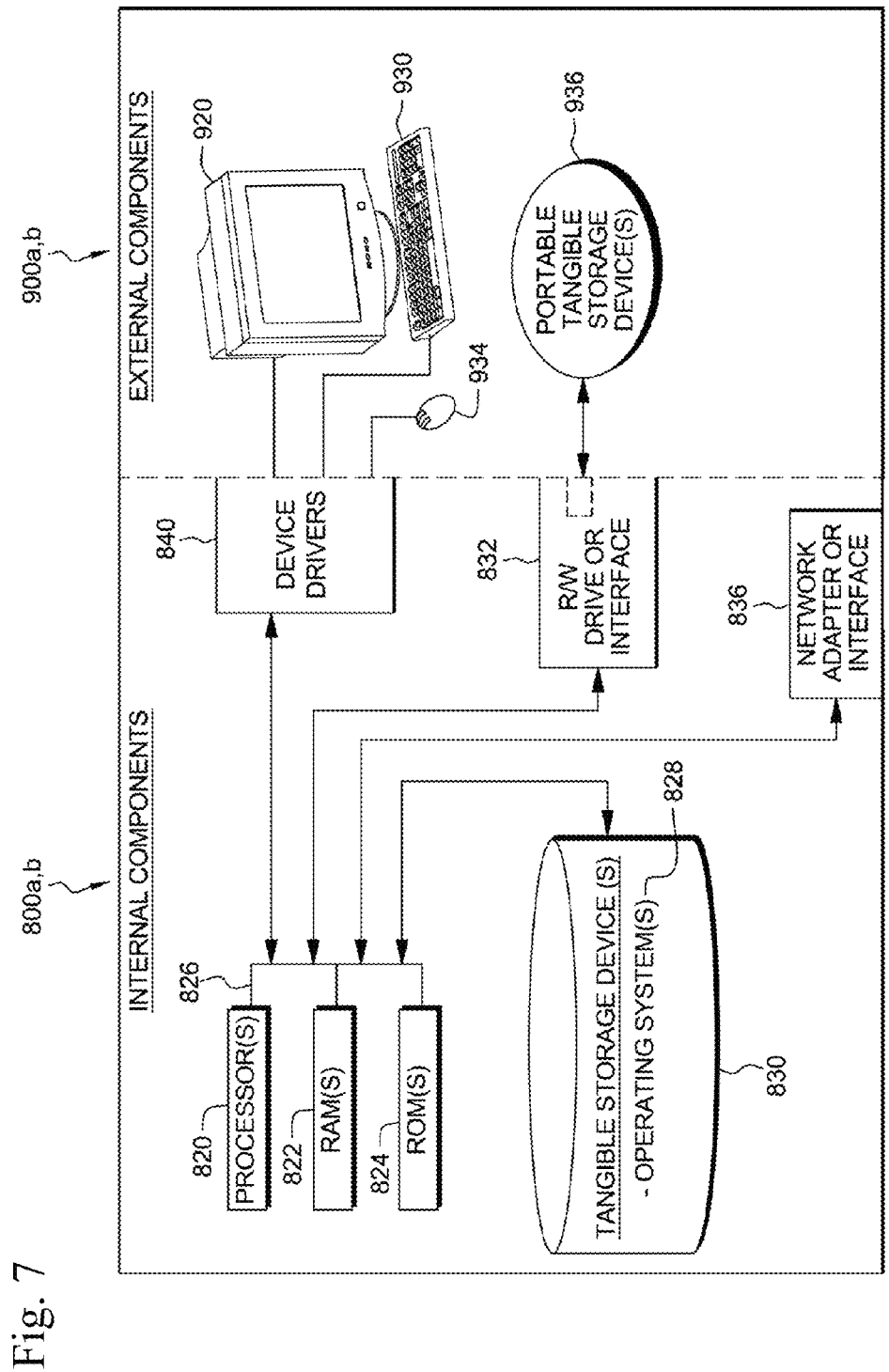
FIG. 7 illustrates internal and external components of a client computer and a server computer in which illustrative embodiments may be implemented.

Program code, reference epigenetic maps, Kohonen maps, and programs such as an epigenetic map to reference epigenetic map compare program 67 and a cohort system program 66 may be stored on at least one of one or more computer-readable tangible storage devices 830 shown in FIG. 7, on at least one of one or more portable computer-readable tangible storage devices 936 as shown in FIG. 7, or repository 53 connected to network 50, or downloaded to a data processing system or other device for use. For example, program code, reference epigenetic maps, Kohonen maps, epigenetic map to reference epigenetic map compare program 67, and a cohort system program 66 may be stored on at least one of one or more tangible storage devices 830 on server computer 54 and downloaded to client computer 52 over network 50 for use on client computer 52. Alternatively, server computer 54 can be a web server, and the program code, reference epigenetic maps, Kohonen maps, and programs such as an epigenetic map to reference epigenetic map compare program 67 and a cohort system program 66 may be stored on at least one of the one or more tangible storage devices 830 on server computer 54 and accessed on client computer 52. Epigenetic map to reference epigenetic map compare program 67 and cohort system program 66 can be accessed on client computer 52 through interface 70. In other exemplary embodiments, the program code, reference epigenetic maps, Kohonen maps, and programs such as an epigenetic map to reference epigenetic map compare program 67 and a cohort system program 66 may be stored on at least one of one or more computer-readable tangible storage devices 830 on client computer 52 or distributed between two or more servers.

In the depicted example, network data processing system 51 is a combination of a number of computers and servers, with network 50 representing the Internet—a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 51 also may be implemented as a number of different types of networks, such as, for example, an intranet, local area network (LAN), or a wide area network (WAN). FIG. 1 is intended as an example, and not as an architectural limitation, for the different illustrative embodiments.

Figure 2:
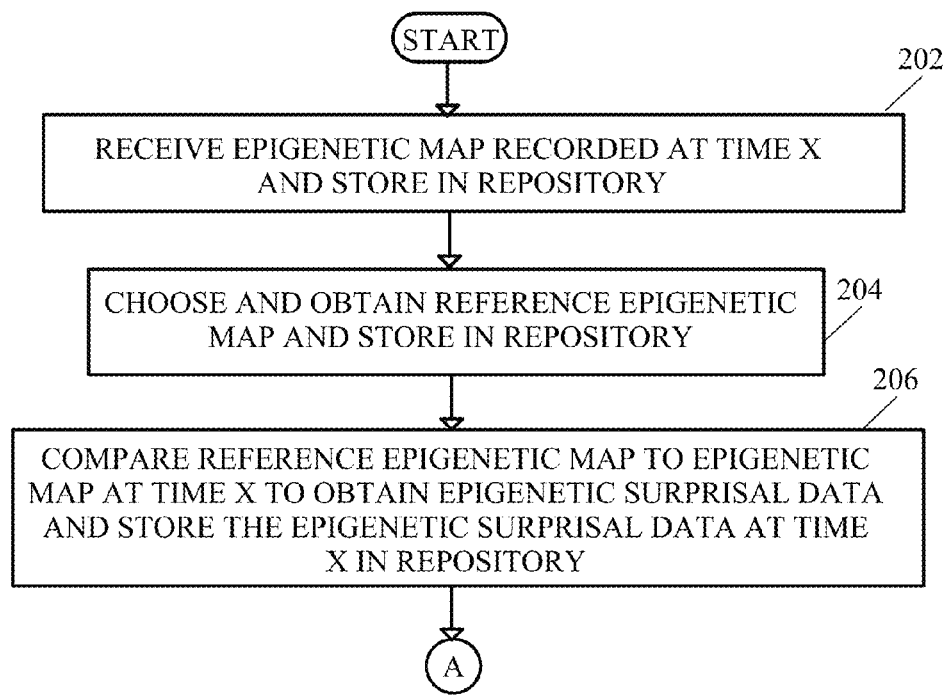
FIG. 2 shows a flowchart of a method of building a repository of epigenetic surprisal data at different time points.

FIG. 2 shows a flowchart of a method of building a repository of epigenetic surprisal data at different time points.

In a first step, an epigenetic map of an organism recorded at a given time (represented by time x) is received, and stored in a repository at a source (step 202), for example in repository 53, by the epigenetic map to reference epigenetic map compare program 67 as shown in FIG. 1. The designation "x" may be any number or other designation desired, for example an arbitrary integer, or a date or time indicator, etc. The organism may be a fungus, microorganism, human, animal or plant.

Based on the organism from which the epigenetic map is derived, an epigenetic map to reference epigenetic map compare program 67 chooses and obtains at least one reference epigenetic map, and stores the reference epigenetic map in a repository (step 204). Alternatively, the epigenetic map to reference epigenetic map compare program 67 may receive an input from a user regarding what specific reference epigenetic map is to be chosen and obtained.

A reference epigenetic map is an epigenetic map database which includes numerous epigenetic maps combined into one map. The details of the epigenetic maps may not represent any one specific individual's epigenetic map of their genome. They serve as a starting point for broad comparisons across a specific species, since the basic set of genes and genomic regulator regions that control the development and maintenance of the biological structure and processes are all essentially the same within a species, and the epigenetic modifications that take place may be similar. In other words, the reference epigenetic map can be a representative example of a species' epigenetic modifications of their genome.

Alternatively, the reference epigenetic map may be derived from the same individual, or a related individual, to the organism from which the epigenetic map was derived at time x (step 202). The reference epigenetic map may have been stored in a repository and derived from the individual at a time prior to time x.

The reference epigenetic map may be tailored depending on the analysis that may take place after obtaining the epigenetic surprisal data. For example, the epigenetic map to reference epigenetic map compare program 67 can limit the comparison to specific genes of the reference epigenetic map, ignoring other gene modifications that may occur in specific populations of a species.

The epigenetic map to reference epigenetic map compare program 67 compares the at least one epigenetic map at time x to the reference epigenetic map to obtain epigenetic surprisal data and stores only the epigenetic surprisal data in a repository 53 (step 206). The epigenetic surprisal data is defined as at least one epigenetic modification difference that provides an "unexpected value" relative to the normally expected value of the reference epigenetic map or epigenetic baseline surprisal data. In other words, the epigenetic surprisal data contains at least one epigenetic modification difference present when comparing the epigenetic map to the reference epigenetic map or to epigenetic baseline surprisal data. The epigenetic surprisal data that is actually stored in the repository preferably includes a location of the epigenetic modification difference within the reference epigenetic map.

Steps 202-206 repeat as epigenetic maps of organisms and specific individuals of organisms are received at different times. The epigenetic surprisal data at different times are stored in the repository.

Figure 3:
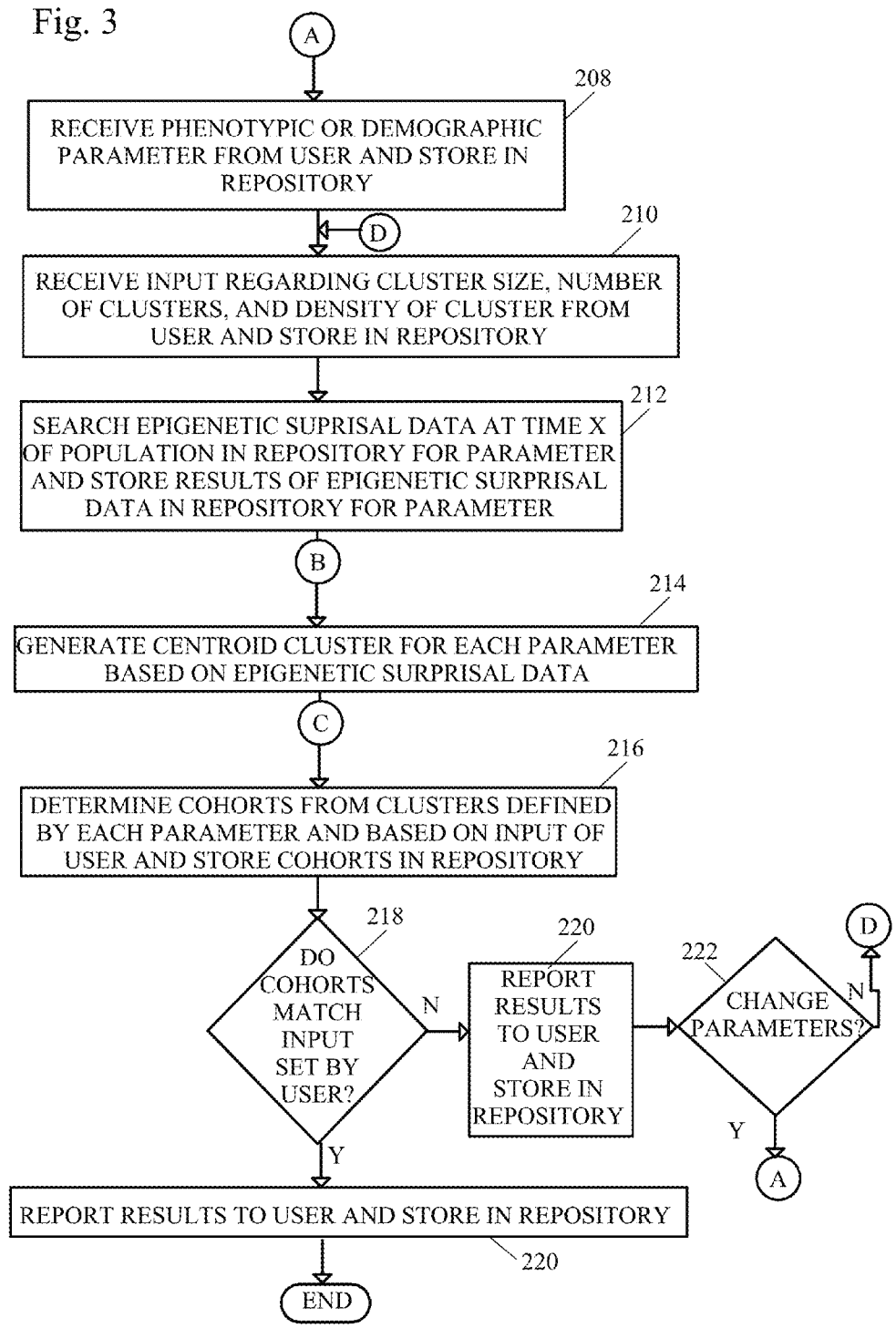
FIG. 3 shows a flowchart of a method of generating epigenetic cohorts through clustering of epigenetic surprisal data based on parameters such as demographics and phenotypic characteristics.

FIG. 3 shows a method of generating epigenetic cohorts for a specific time period through clustering of epigenetic surprisal data at a specific time based on parameters such as demographics and phenotypic characteristics. By using epigenetic surprisal data at a specific time with parameters, such as demographics and phenotypic traits, a user, for example, a researcher, can determine the effect living in a certain place can have in relation to people's epigenetics and in relation to a specific type of treatment for a disease.

After the epigenetic surprisal data has generated, for example using steps 202-206 in FIG. 2, a phenotypic and/or demographic parameter is received from a user and stored in a repository (step 208). A demographic parameter is any statistical characteristic of a population. The demographic parameter can include gender, race, age, disabilities, mobility and others. By including a demographic parameter, the user can allow traits of a population of a region and the culture of the people there to be considered. A phenotypic parameter is an observable physical or biochemical characteristics of an organism, as determined by both genetic makeup and environmental influences. The phenotypic parameter is the expression of a specific trait, for example stature or blood type, based on genetic and environmental influences.

An input regarding the cluster size, number of clusters and density of the cluster is received from the user and stored in a repository (step 210). This input is used to determine the characteristics of the cohorts to be generated in a later step.

Then, the epigenetic surprisal data at time x generating in steps 202-206 is searched for the user defined parameter and the matches are stored in a repository (step 212), for example using the cohort system program 66 of FIG. 1. The searching may be carried out through data mining.

A centroid cluster based on each parameter is generated based on the epigenetic surprisal data by populating the cluster based on the matches of the parameter with the epigenetic surprisal data at a specific time period (step 214). The generation of the centroid is generated by the steps shown in FIG. 4.

Figure 4:
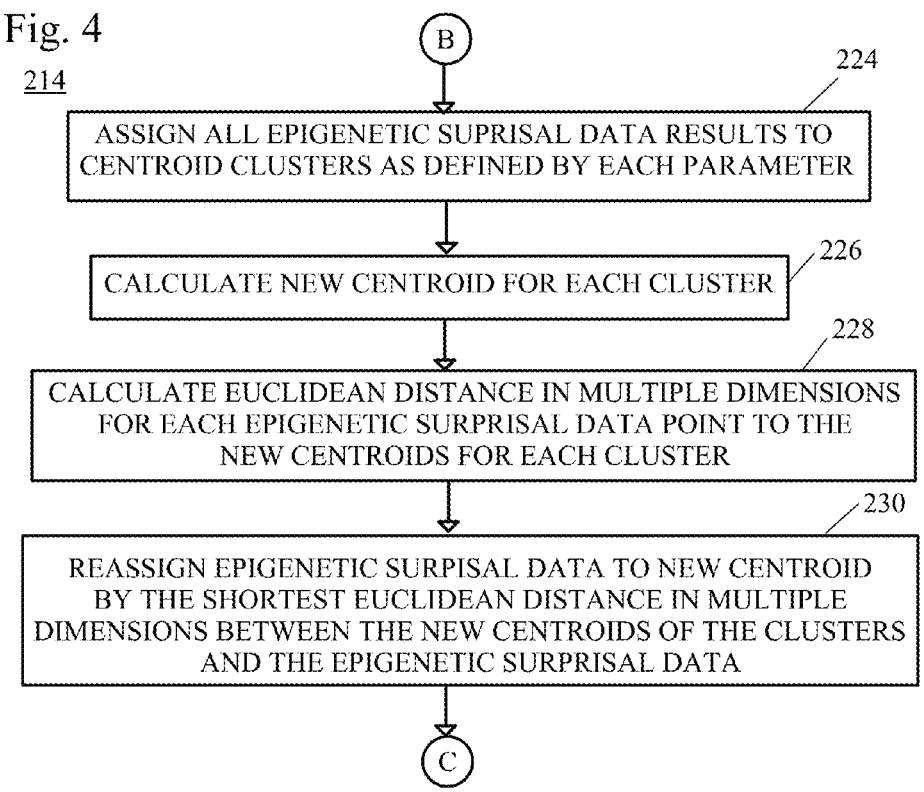
FIG. 4 shows a flowchart of the steps associated with generating a center cluster for each parameter based on epigenetic surprisal data.

Referring to FIG. 4, all epigenetic surprisal data results are assigned to centroid clusters defined by each parameter (step 224), for example a phenotypic or demographic parameter. Once all of the epigenetic surprisal data matches have been assigned to centroid clusters first chosen, a new centroid is calculated for each cluster (step 226). The calculation of the new centroid after all of the points of epigenetic surprisal data has been assigned typically moves the centroid and causes the assignment of the points to the cluster to now be inaccurate. So, a Euclidean distance in multiple dimensions is calculated for each epigenetic surprisal data match to the new centroids for each cluster (step 228). The epigenetic surprisal data is reassigned to the new centroid by the shortest Euclidean distance in multiple dimensions between the new centroids of the clusters and the epigenetic surprisal data (step 230).

After step 214 of generating centroid clusters based on each parameter, at least two epigenetic cohorts for a specific time period from the clusters defined by each parameter and based on input of the user are determined and the epigenetic cohorts are stored in the repository (step 216), for example repository 53 of FIG. 1. The at least two epigenetic cohorts that may be generated are a control cohort and a treatment cohort. A centroid for each cluster based on each parameter is generated based on the epigenetic surprisal data by populating the cluster based on the matches of the parameter with the epigenetic surprisal data at a specific time period.

If the cohorts match the input set by the user, for example the cluster size, the number of clusters, and density of clusters (step 218), then the results are stored in a repository and reported to the user (step 220) and the method ends.

If the cohorts do not match the input set by the user, the results are stored in a repository and reported to the user (step 220). If the user wishes to change the parameters to alter the cohorts (step 222), the method returns to step 208 of receiving a phenotypic and/or demographic parameter from the user. If the user does not want to change parameters to alter the cohorts (step 222), the method returns to step 210 to receive input regarding the cluster size, number of clusters and density of clusters.

Figure 5:
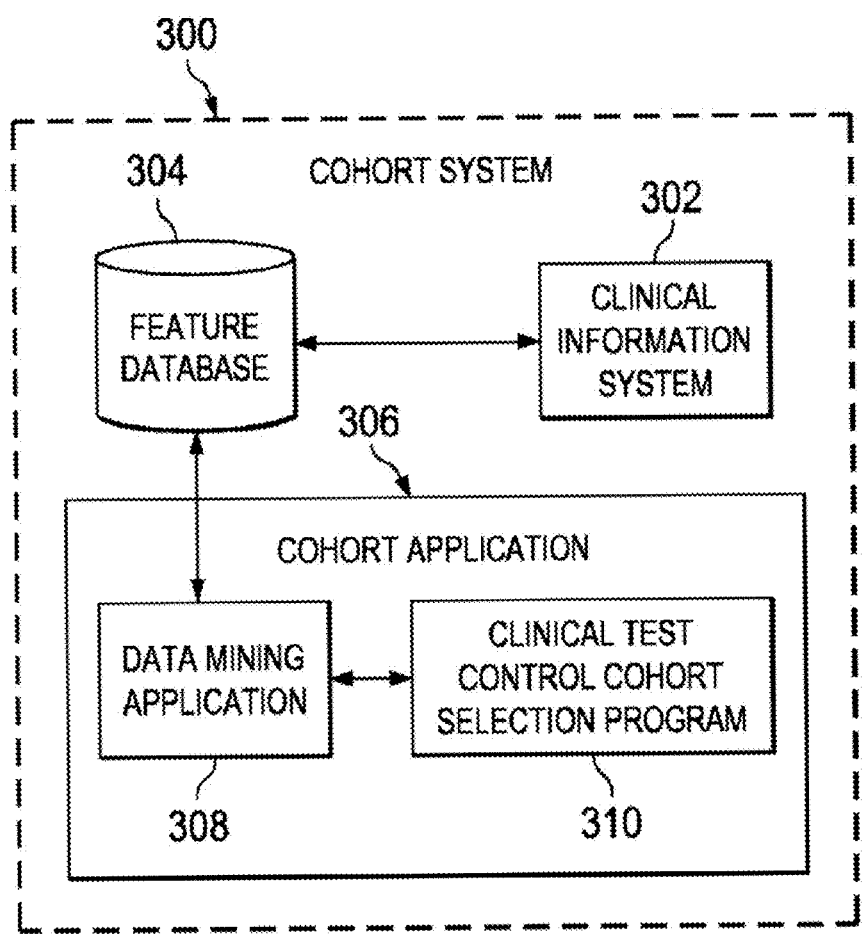
FIG. 5 shows block diagram of a system for generating control cohorts in accordance with an illustrative embodiment.

FIG. 5 shows a block diagram of a system for generating epigenetic surprisal data control cohorts in accordance with an illustrative embodiment. Cohort system 300 is a system for generating epigenetic cohorts, including control cohorts and may use cohort system program 66 as shown in FIG. 1 to control and operate the cohort system and its associated elements and programs. Cohort system 300 includes clinical information system (CIS) 302, feature database 304, and cohort application 306. Each component of cohort system 300 may be interconnected via a network, such as network 50 of FIG. 1. Cohort application 306 further includes data mining application 308 and clinical test control cohort selection program 310.

Clinical information system 302 is a management system for managing patient data. This data may include, for example, demographic data, family health history data, vital signs, laboratory test results, drug treatment history, admission-discharge-treatment (ADT) records, co-morbidities, modality images, genetic data, epigenetic surprisal genetic data, other phenotypic data, and other patient data. Clinical information system 302 may be executed by a computing device, such as server computer 54 or client computer 52 of FIG. 1. Clinical information system 302 may also include information about a population of patients as a whole. Such information may disclose patients who have agreed to participate in medical research but who are not participants in a current study. Clinical information system 302 includes medical records for acquisition, storage, manipulation, and distribution of clinical information for individuals and organizations. Clinical information system 302 is scalable, allowing information to expand as needed. Clinical information system 302 may also include information sourced from pre-existing systems, such as pharmacy management systems, laboratory management systems, and radiology management systems.

Feature database 304 is a database in a repository, such as repository 53 of FIG. 1. Feature database 304 is populated with data from clinical information system 302. Feature database 304 includes patient data in the form of attributes. Attributes define features, variables, and characteristics of each patient. Attributes may be associated with specific parameters set by the user. For example, if a demographic parameter of "living in New York" is specified by a user, this characteristic of the patient may be easily searched for in the feature database 304. The most common attributes may include gender, age, disease or illness, and state of the disease. These attributes may be used in steps 212 and 214 of FIG. 3 and step 224 of FIG. 4 when searching the population for matches to parameters set by a user.

Cohort application 306 is a program for selecting control cohorts. Cohort application 306 is executed by a computing device, such as server computer 54 or client computer 52 of FIG. 1. Data mining application 308 is a program that provides data mining functionality on feature database 304 and other interconnected databases. In one example, data mining application 308 may be a program, such as DB2 Intelligent Miner produced by International Business Machines Corporation. Data mining is the process of automatically searching large volumes of data for patterns. Data mining may be further defined as the nontrivial extraction of implicit, previously unknown, and potentially useful information from data. Data mining application 308 uses computational techniques from statistics, information theory, machine learning, and pattern recognition.

Particularly, data mining application 308 extracts useful information from feature database 304. Data mining application 308 allows users to select data, analyze data, show patterns, sort data, determine relationships, and generate statistics. Data mining application 308 may be used to cluster records in feature database 304 based on specified parameters, such as demographic or phenotypic parameters to generate central and may be used to implement steps 214 and 216 of FIG. 3 and steps 224 through 230 of FIG. 4. Data mining application 308 searches the records for parameters set by the user, and groups the related records or members accordingly for display or analysis to the user. This grouping process is referred to as clustering. The results of clustering show the number of detected clusters and the attributes that make up each cluster. Clustering is further described with respect to FIGS. 6A and 6B.

For example, data mining application 308 may be able to group patient records to show the effect of a new sepsis blood infection medicine. Currently, about 35 percent of all patients with the diagnosis of sepsis die. Patients entering an emergency department of a hospital who receive a diagnosis of sepsis, and who are not responding to classical treatments, may be recruited to participate in a drug trial. A statistical control cohort of similarly ill patients could be developed by cohort system 300, using records from historical patients, patients from another similar hospital, and patients who choose not to participate. Potential features to produce a clustering model could include age, co-morbidities, gender, surgical procedures, number of days of current hospitalization, $O_2$ blood saturation, blood pH, blood lactose levels, bilirubin levels, blood pressure, respiration, mental acuity tests, epigenetic surprisal data, living conditions prior to being diagnosed with sepsis, and urine output.

Data mining application 308 may use a clustering technique or model known as a Kohonen feature map neural network or neural clustering. Kohonen feature maps specify a number of clusters and the maximum number of passes through the data, for example provided by the input of the user as shown in step 210 of FIG. 3. The number of clusters must be between one and the number of records in the treatment cohort. The greater the number of clusters, the better the comparisons can be made between the treatment and the control cohort. Clusters are natural groupings of patient records based on the specified features, parameters or attributes. For example, a user may request that data mining application 308 generate eight clusters in a maximum of ten passes. The main task of neural clustering is to find a center or centroid for each cluster. The centroid is also called the cluster prototype. Scores are generated based on the distance between each patient record and each of the cluster prototypes. Scores closer to zero have a higher degree of similarity to the cluster prototype. The higher the score, the more dissimilar the record is from the cluster prototype.

All inputs to a Kohonen feature map must be scaled from 0.0 to 1.0. In addition, categorical values must be converted into numeric codes for presentation to the neural network. Conversions may be made by methods that retain the ordinal order of the input data, such as discrete step functions or bucketing of values. Each record is assigned to a single cluster, but by using data mining application 308, a user may determine a record's Euclidean dimensional distance for all cluster prototypes, as in step 228 of FIG. 4. Clustering is performed for the treatment cohort. Clinical test control cohort selection program 310 minimizes the sum of the Euclidean distances between the individuals or members in the treatment cohorts and the control cohort, as also described in step 230 of FIG. 4. Clinical test control cohort selection program 310 may incorporate an integer programming model. This program may be programmed in International Business Machine Corporation products, such as Mathematical Programming System eXtended (MPSX), the IBM Optimization Subroutine Library, or the open source GNU Linear Programming Kit. The illustrative embodiments minimize the summation of all records/cluster prototype Euclidean distances from the potential control cohort members to select the optimum control cohort.

Figure 6A:
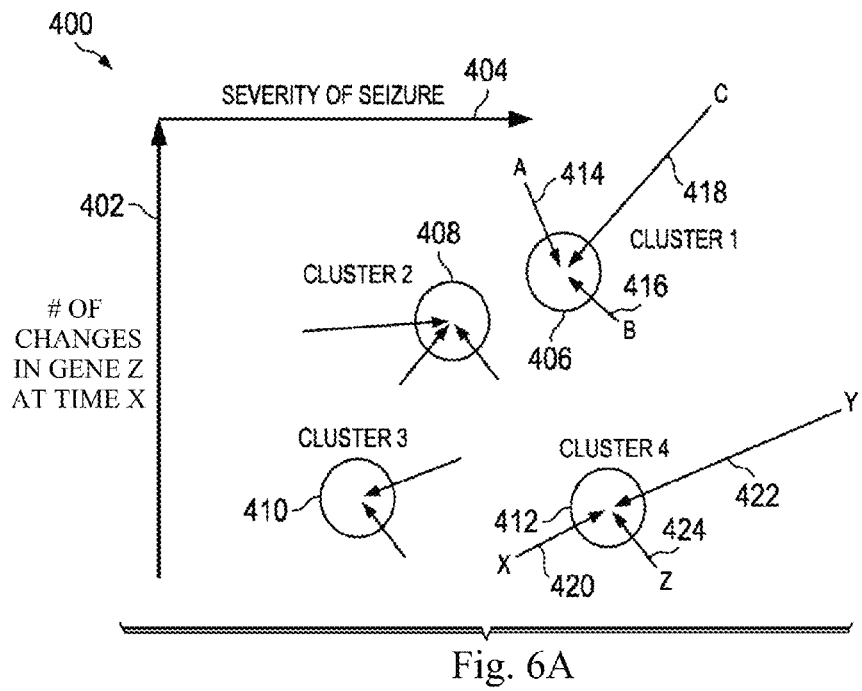
FIGS. 6A-6B are graphical illustrations of clustering in accordance with an illustrative embodiment.
Figure 6B:
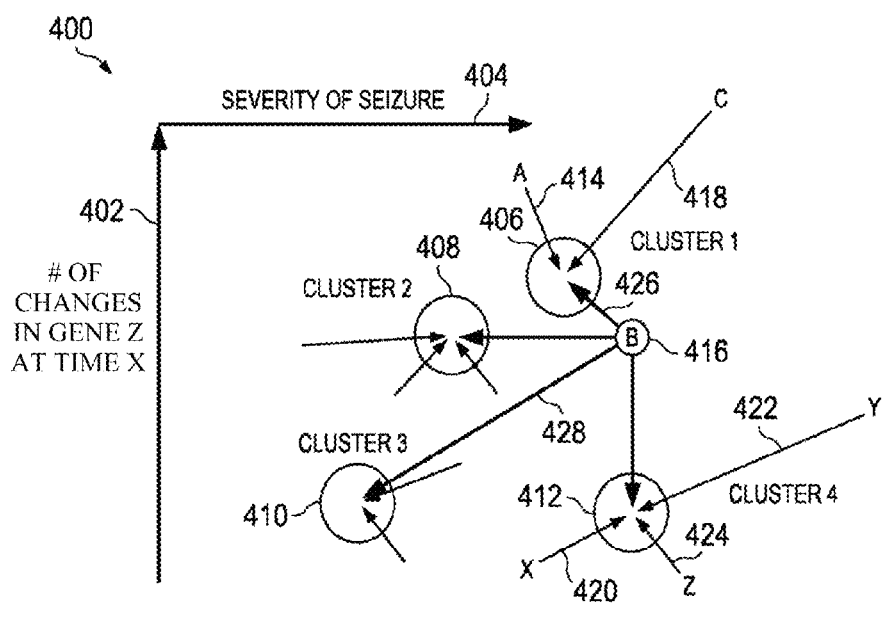

FIGS. 6A-6B are graphical illustrations of clustering in accordance with an illustrative embodiment. Feature map 400 of FIG. 6A is a self-organizing map (SOM) and is a subtype of artificial neural networks. Feature map 400 is trained using unsupervised learning to produce a low-dimensional representation of the training samples while preserving the topological properties of the input space. This makes feature map 400 especially useful for visualizing high-dimensional data, including cohorts and clusters.

In one illustrative embodiment, feature map 400 is a Kohonen Feature Map neural network. Feature map 400 uses a process called self-organization to group similar patient records together. Feature map 400 may use various dimensions. In this example, feature map 400 is a two-dimensional feature map including number of changes to gene z at time x (e.g. epigenetic surprisal data) 402 and severity of seizure 404. Feature map 400 may include as many dimensions as there are features, such as age, gender, phenotypic data, demographic data, and severity of illness. Feature map 400 also includes cluster 1 406, cluster 2 408, cluster 3 410, and cluster 4 412. The clusters are the result of using feature map 400 to group individual patients based on the features. The clusters are self-grouped local estimates of all data or patients being analyzed based on competitive learning. When a training sample of patients is analyzed by data mining application 308 of FIG. 5, each patient is grouped into clusters where the clusters are weighted functions that best represent natural divisions of all patients based on the specified features.

The user may choose to specify the number of clusters and the maximum number of passes through the data. These parameters control the processing time and the degree of granularity used when patient records are assigned to clusters. The primary task of neural clustering is to find a center or centroid for each cluster. The centroid is also called the cluster prototype. For each record in the input patient data set, the neural clustering data mining program computes the cluster prototype that is the closest to the records. For example, patient record A 414, patient record B 416, and patient record C 418 are grouped into cluster 1 406. Additionally, patient record X 420, patient record Y 422, and patient record Z 424 are grouped into cluster 4 412.

FIG. 6B further illustrates how the score for each data record is represented by the Euclidean distance from the cluster prototype. The higher the score, the more dissimilar the record is from the particular cluster prototype. With each pass over the input patient data, the centers are adjusted so that a better quality of the overall clustering model is reached. To score a potential control cohort for each patient record, the Euclidian distance is calculated from each cluster prototype. This score is passed along to an integer programming system in clinical test control cohort selection program 310 of FIG. 5.

For example, patient B 416 is scored into the cluster prototype or center of cluster 1 406, cluster 2 408, cluster 3 410 and cluster 4 412. A Euclidean distance between patient B 416 and cluster 1 406, cluster 2 408, cluster 3 410 and cluster 4 412 is shown. In this example, distance 1 426, separating patient B 416 from cluster 1 406, is the closest. Distance 3 428, separating patient B 416 from cluster 3 410, is the furthest. These distances indicate that cluster 1 406 is the best fit.

FIG. 7 illustrates internal and external components of client computer 52 and server computer 54 in which illustrative embodiments may be implemented. In FIG. 7, client computer 52 and server computer 54 include respective sets of internal components 800a, 800b, and external components 900a, 900b. Each of the sets of internal components 800a, 800b includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, epigenetic map to reference epigenetic map compare program 67 and cohort system program 66 are stored on one or more of the computer-readable tangible storage devices 830 for execution by one or more of the processors 820 via one or more of the RAMs 822 (which typically include cache memory). In the embodiment illustrated in FIG. 7, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b also includes a R/W drive or interface 832 to read from and write to one or more portable computer-readable tangible storage devices 936 such as a CD-ROM, DVD, memory stick, magnetic tape, magnetic disk, optical disk or semiconductor storage device. Epigenetic map to reference epigenetic map compare program 67 and cohort system program 66 can be stored on one or more of the portable computer-readable tangible storage devices 936, read via R/W drive or interface 832 and loaded into hard drive 830.

Each set of internal components 800a, 800b also includes a network adapter or interface 836 such as a TCP/IP adapter card. Epigenetic map to reference epigenetic map compare program 67 and cohort system program 66 can be downloaded to client computer 52 and server computer 54 from an external computer via a network (for example, the Internet, a local area network or other, wide area network) and network adapter or interface 836. From the network adapter or interface 836, an epigenetic map to reference epigenetic map compare program 67 and a cohort system program 66 are loaded into hard drive 830. The network may comprise copper wires, optical fibers, wireless transmission, routers, firewalls, switches, gateway computers and/or edge servers.

Each of the sets of external components 900a, 900b includes a computer display monitor 920, a keyboard 930, and a computer mouse 934. Each of the sets of internal components 800a, 800b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Epigenetic map to reference epigenetic map compare program 67 and cohort system program 66 can be written in various programming languages including low-level, high-level, object-oriented or non object-oriented languages. Alternatively, the functions of an epigenetic map to reference epigenetic map compare program 67 and a cohort system program 66 can be implemented in whole or in part by computer circuits and other hardware (not shown).

Based on the foregoing, a computer system, method and program product have been disclosed for generating epigenetic cohorts through clustering of epigenetic surprisal data based on parameters such as demographics and phenotypic characteristics. However, numerous modifications and substitutions can be made without deviating from the scope of the present invention. Therefore, the present invention has been disclosed by way of example and not limitation.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method of generating epigenetic cohorts for a specific time period through clustering of epigenetic surprisal data at a specific time comprising:
   a computer receiving a phenotypic and/or demographic parameter and a cluster characteristics input comprising a cluster size, a number of clusters and a density of the cluster from a user;
   the computer searching the epigenetic surprisal data at a specific time associated with a patient for the phenotypic and/or demographic parameter and storing matches of the parameter with the epigenetic surprisal data in a repository;
   the computer generating a cluster comprising a centroid for each parameter by populating the cluster based on the matches of the parameter with the epigenetic surprisal data at a specific time period;
   the computer determining results of at least two epigenetic cohorts for a specific time period, a control cohort and a treatment cohort, from the cluster for each parameter and based on the input from the user; and
   wherein when the cohorts do not match the input of the user, reporting a null result determined to the user and return to the step of the computer receiving a phenotypic and/or demographic parameter from a user and a cluster characteristics input to refine the parameters.

2. The method of claim 1, further comprising prior to the computer receiving a parameter and a cluster characteristics input, the computer:
   receiving an epigenetic map at time x of an organism comprising epigenetic modifications;
   comparing the epigenetic map at time x to a reference epigenetic map, to find differences where epigenetic modifications of the organism at time x are different from the epigenetic modifications of the reference epigenetic map; and
   the computer using the differences to create and store epigenetic surprisal data in a repository, the epigenetic surprisal data comprising a location of the epigenetic modification, the time in which the epigenetic modification was collected and the type of epigenetic modification.

3. The method of claim 1, wherein the step of the computer generating a cluster comprising a centroid for each parameter by populating the cluster based on the matches of the parameter with the epigenetic surprisal data at a specific time period comprises:
   the computer assigning all of the epigenetic surprisal data matches to the centroid of the cluster as defined by each parameter;
   the computer calculating a new centroid for each cluster;
   the computer calculating a Euclidean distance in multiple dimensions for each epigenetic surprisal data match to the new centroid for each cluster; and
   the computer reassigning the epigenetic surprisal data matches to the new centroid of each cluster based on the shortest calculated Euclidean distance to the new centroid for each cluster.

4. The method of claim 1, wherein the step of the computer searching the epigenetic surprisal data at a specific time associated with a patient for the phenotypic and/or demographic parameter is performed by a data mining application.

5. The method of claim 1, wherein the step of the computer determining results of at least two epigenetic cohorts for a specific time period from the cluster for each parameter and based on the input from the user further comprises: generating a feature map to form treatment cohorts.

6. The method of claim 5, wherein the feature map is a Kohonen feature map.

7. A computer program product for generating epigenetic cohorts for a specific time period through clustering of epigenetic surprisal data at a specific time comprising:
   one or more computer-readable, non-transitory tangible storage devices;
   program instructions, stored on at least one of the one or more storage devices, to receive a phenotypic and/or demographic parameter and a cluster characteristics input comprising a cluster size, a number of clusters and a density of the cluster from a user;
   program instructions, stored on at least one of the one or more storage devices, to search the epigenetic surprisal data at a specific time associated with a patient for the phenotypic and/or demographic parameter and store matches of the parameter with the epigenetic surprisal data in a repository;
   program instructions, stored on at least one of the one or more storage devices, to generate a cluster comprising a centroid for each parameter by populating the cluster based on the matches of the parameter with the epigenetic surprisal data at a specific time period;
   program instructions, stored on at least one of the one or more storage devices, to determine results of at least two epigenetic cohorts for a specific time period, a control cohort and a treatment cohort, from the cluster for each parameter and based on the input from the user; and
   wherein when the cohorts do not match the input of the user, program instructions, stored on at least one of the one or more storage devices, to report a null result of the cohorts determined to the user and return to program instructions, stored on at least one of the one or more storage devices, to receive a phenotypic and/or demographic parameter from a user and a cluster characteristics input to refine the parameters.

8. The computer program product of claim 7, further comprising prior to the program instructions, stored on at least one of the one or more storage devices, to receive a parameter and a cluster characteristics input, program instructions, stored on at least one of the one or more storage devices, to:
   receive an epigenetic map at time x of an organism comprising epigenetic modifications;
   compare the epigenetic map at time x to a reference epigenetic map, to find differences where epigenetic modifications of the organism at time x are different from the epigenetic modifications of the reference epigenetic map; and use the differences to create and store epigenetic surprisal data in a repository, the epigenetic surprisal data comprising a location of the epigenetic modification, the time in which the epigenetic modification was collected and the type of epigenetic modification.

9. The computer program product of claim 7, wherein the program instructions, stored on at least one of the one or more storage devices, to generate a cluster comprising a centroid for each parameter by populating the cluster based on the matches of the parameter with the epigenetic surprisal data at a specific time period comprises:

assigning all of the epigenetic surprisal data matches to the centroid of the cluster as defined by each parameter;

calculating a new centroid for each cluster;

calculating a Euclidean distance in multiple dimensions for each epigenetic surprisal data match to the new centroid for each cluster; and reassigning the epigenetic surprisal data matches to the new centroid of each cluster based on the shortest calculated Euclidean distance to the new centroid for each cluster.

10. The computer program product of claim 7, wherein the program instructions, stored on at least one of the one or more storage devices, to search the epigenetic surprisal data at a specific time associated with a patient for the phenotypic and/or demographic parameter is performed by a data mining application.

11. The computer program product of claim 7, wherein the program instructions, stored on at least one of the one or more storage devices, to determine results of at least two epigenetic cohorts for a specific time period from the cluster for each parameter and based on the input from the user further comprises program instructions, stored on at least one of the one or more storage devices, to generate a feature map to form treatment cohorts.

12. The computer program product of claim 11, wherein the feature map is a Kohonen feature map.

13. A system for generating epigenetic cohorts for a specific time period through clustering of epigenetic surprisal data at a specific time comprising:

one or more processors, one or more computer-readable memories and one or more computer-readable, tangible storage devices;

program instructions, stored on at least one of the one or more storage devices for execution by at least one of the one or more processors via at least one of the one or more memories, to receive a phenotypic and/or demographic parameter and a cluster characteristics input comprising a cluster size, a number of clusters, and a density of the cluster from a user;

program instructions, stored on at least one of the one or more storage devices for execution by at least one of the one or more processors via at least one of the one or more memories, to search the epigenetic surprisal data at a specific time associated with a patient for the phenotypic and/or demographic parameter and store matches of the parameter with the epigenetic surprisal data in a repository;

program instructions, stored on at least one of the one or more storage devices for execution by at least one of the one or more processors via at least one of the one or more memories, to generate a cluster comprising a centroid for each parameter by populating the cluster based on the matches of the parameter with the epigenetic surprisal data at a specific time period;

program instructions, stored on at least one of the one or more storage devices for execution by at least one of the one or more processors via at least one of the one or more memories, to determine at least two epigenetic cohorts for a specific time period, a control cohort and a treatment cohort, from the cluster for each parameter and based on the input from the user; and wherein when the cohorts do not match the input of the user, program instructions, stored on at least one of the one or more storage devices for execution by at least one of the one or more processors via at least one of the one or more memories, to report a null result determined to the user and return to program instructions, stored on at least one of the one or more storage devices, to receive a phenotypic and/or demographic parameter from a user and a cluster characteristics input to refine the parameters.

14. The system of claim 13, further comprising prior to the program instructions, stored on at least one of the one or more storage devices for execution by at least one of the one or more processors via at least one of the one or more memories, to receive a parameter and a cluster characteristics input, program instructions, stored on at least one of the one or more storage devices for execution by at least one of the one or more processors via at least one of the one or more memories, to:

receive an epigenetic map at time x of an organism comprising epigenetic modifications;

compare the epigenetic map at time x to a reference epigenetic map, to find differences where epigenetic modifications of the organism at time x are different from the epigenetic modifications of the reference epigenetic map; and use the differences to create and store epigenetic surprisal data in a repository, the epigenetic surprisal data comprising a location of the epigenetic modification, the time in which the epigenetic modification was collected and the type of epigenetic modification.

15. The system of claim 13, wherein the program instructions, stored on at least one of the one or more storage devices for execution by at least one of the one or more processors via at least one of the one or more memories, to generate a cluster comprising a centroid for each parameter by populating the cluster based on the matches of the parameter with the epigenetic surprisal data at a specific time period comprises:

assigning all of the epigenetic surprisal data matches to the centroid of the cluster as defined by each parameter;

calculating a new centroid for each cluster;

calculating a Euclidean distance in multiple dimensions for each epigenetic surprisal data match to the new centroid for each cluster; and reassigning the epigenetic surprisal data matches to the new centroid of each cluster based on the shortest calculated Euclidean distance to the new centroid for each cluster.

16. The system of claim 13, wherein the program instructions, stored on at least one of the one or more storage devices for execution by at least one of the one or more processors via at least one of the one or more memories, to search the epigenetic surprisal data at a specific time associated with a patient for the phenotypic and/or demographic parameter is performed by a data mining application.

17. The system of claim 13, wherein the program instructions, stored on at least one of the one or more storage devices for execution by at least one of the one or more processors via at least one of the one or more memories, to determine results at least two epigenetic cohorts for a specific time period from the cluster for each parameter and based on the input from the user further comprises program instructions, stored on at least one of the one or more storage devices for execution by at least one of the one or more processors via at least one of the one or more memories, to generate a feature map to form treatment cohorts.

18. The system of claim 17, wherein the feature map is a Kohonen feature map.

* * * * *